United States Patent [19]

Messenheimer

[11] Patent Number: 5,009,235
[45] Date of Patent: Apr. 23, 1991

[54] URINE SPECIMEN COLLECTING METHOD USING A VEHICLE

[76] Inventor: Ronald L. Messenheimer, 11909 Trailridge Dr., Potomac, Md. 20854

[21] Appl. No.: 394,719

[22] Filed: Aug. 16, 1989

[51] Int. Cl.$^5$ .............................................. A61B 5/00
[52] U.S. Cl. ................................... 128/760; 296/24.1
[58] Field of Search .............. 128/760; 296/24.1, 156, 296/164

[56] References Cited

U.S. PATENT DOCUMENTS

| | | | |
|---|---|---|---|
| 2,817,846 | 12/1957 | Stift | 296/24.1 |
| 3,923,040 | 12/1975 | Beach | 128/760 |
| 4,094,648 | 6/1978 | Seeley | 128/760 |
| 4,181,347 | 1/1980 | Clark | 296/24.1 |
| 4,428,384 | 1/1984 | Raitto | 128/760 |
| 4,550,946 | 11/1985 | Hanemaayer | 292/24.1 |

Primary Examiner—Max Hindenburg

[57] ABSTRACT

A vehicle (10) especially configured for collecting without observation urine specimens to be tested for the presence of illegal drugs, which has multiple privacy rooms (12) each with a urine disposal device (14). Each privacy room prevents access to liquids or other substances which can be used to substitute for or adulterate a donor's urine specimen. The collection site person is at a station (20) that is near a supply of containers, a secure receptacle (18) for temporary locked storage of filled containers and special outer garment and valuable article storage areas (24, 26). The vehicle may be towed as a trailer or self-powered and does not require external permanent water supply or drain connections.

3 Claims, 2 Drawing Sheets

URINE SPECIMEN COLLECTING METHOD USING A VEHICLE

This invention relates to a method for collecting urine specimens in a vehicle especially adapted for urine specimen collection as part of a urine analysis test program.

BACKGROUND OF THE INVENTION

As a consequence of drug abuse by employees of government as well as many large organizations including those providing utilities, transportation and heavy manufacturing, there is an urgent need for an efficient collection of urine specimens on a large scale basis. It has been estimated that the current cost to society in the United States due to drug abuse is nearly $100 billion annually. Obtaining urine specimens in a socially acceptable manner from individuals on a mandatory basis presents a number of problems because of cheating by some of those individuals whom the program is designed to identify.

Producing urine specimens for the donor's own purpose and benefit can be done without the types of problems that are encountered when the donor is compelled, perhaps against his will, to deliver a urine specimen to a third party for testing for illegal drugs where unfavorable results may cause loss of employment or other detriment to the individual. In some instances, the urine specimens have been produced in the presence of an observer to prevent cheating. The use of observers is not a preferred practice and it is the purpose of the present invention to avoid this practice.

SUMMARY OF INVENTION

A major object of the invention is to provide a novel vehicle adapted for urine sample collection to detect drug abuse. The vehicle contains multiple privacy rooms and is arranged to permit the collection of urine samples in a strictly controlled environment wherein an untainted urine sample can be obtained with a reasonable level of confidence without objectionable intrusion. To this end the privacy rooms are provided with a toilet or other receptacle for disposal of excess urine and, if necessary other body waste without allowing the donor to have access to liquids or other substances which could be used to substitute for or adulterate the urine sample. A sink may be located outside the privacy room to provide hygienic conditions, and a writing surface is available for assisting in completing necessary paperwork and affixing in the presence of the donor, of a seal on a filled sample container. Outer garment and valuable article storage areas are conveniently located and under the supervision of the collection site person. This vehicle configuration will significantly help prevent adulteration of the urine sample and make the urine collection process a smooth and efficient operation.

Another major object of the invention is to provide a novel method for collecting urine samples on an unobserved basis within a confined structure that is mobile. The urine specimen or sample will be tested for the presence of illegal drugs and/or alcohol. Temporary secure storage of collected specimens is provided prior to shipment to a certified drug testing laboratory.

These and other objects of the invention will become more fully apparent from the claims and from the specification as it proceeds in conjunction with the drawings.

DETAILED DESCRIPTION OF PREFERRED EMBODIMENTS

In carrying out the urine specimen collection procedure in accordance with the present invention, a mobile collection unit 10 is provided which is of a size that can be driven or towed on highways and streets to a location which is convenient to the people to be tested. Thus, the vehicle may be moved to locations such as where the donors are employed, where they reside or any other geographically suitable location. Advance scheduling for one or more specimen donors is arranged to provide for efficient use of the mobile collection unit 10.

Figure 1:
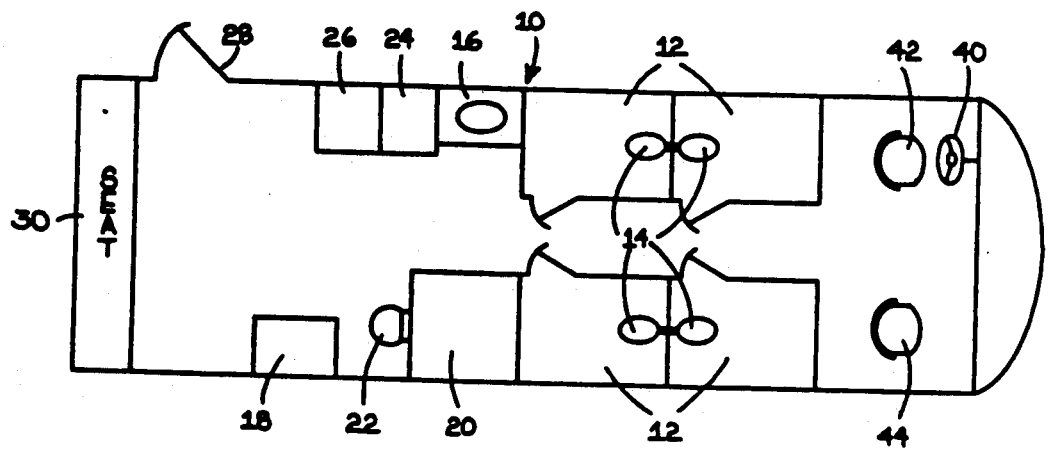
FIG. 1 is a top plan view of a self-propelled motor home modified to have four privacy rooms for simultaneous use and the other features which are unique to the supervised collection of urine samples.

The illustrated mobile collection unit 10 is equipped with four privacy rooms 12, each of which can contain a urine disposal device 14 which may be a toilet, urinal or other receptacle. As shown in FIG. 1, these devices 14 are shown mounted in a back to back relation with a similar device in an adjoining privacy room 12.

In each privacy room 12, private urination can take place. The receptacles 14 are preferably of the type which do not have an accessible reservoir of water which eliminates the need for using a dye to color the water. It should be borne in mind that steps are necessary to prevent the use of substitute liquids such as water, household cleaners, bleach, drain cleaners and the like to contaminate, alter, dilute or otherwise adulterate the urine that is provided in the specimen container.

To this end, the privacy room 12 is preferably not equipped with a lavatory, other handwashing device or other accessible source of water. Where a sink is present, the water is cut off as by a supply valve, tape or security seal. Water that is colored or supplied at a temperature sufficiently below body temperature so that use of such water would be detected by temperature measuring safeguards may be acceptable as specimen integrity enhancement measures.

A lavatory or sink 16 is provided outside of the privacy rooms 12 for hygienic purposes so that it will be available for use after the urine collection container has been sealed. A counter near or adjacent to the sink or at the desk for the collection site person serves as a writing surface to assist in the completion of required paperwork.

Handling of urine collection containers must be documented from the moment of release by the collection site operator, including during possession by the specimen donor, until after the sample is collected and securely stored. In the vehicle, a special repository 18 is provided for temporary secure storage which is under the control of the collection site person who occupies the reception station 20 which may be adjacent to a supply 22 of empty sterile containers. The receptacle 18 is preferably provided with an inlet opening which accepts the urine filled containers and which can only be accessed for removing containers by opening a locked door. A paper trail is provided which identifies each person who handles each sealed urine container. After sealed containers are collected during a work day, the receptacle 18 will be opened to permit the removal of sealed containers for subsequent transport to an approved laboratory together with appropriate paperwork indicating the chain of custody at all times. At this date, only a limited number of approved laboratories are available, and the delivery may be by courier, express or first class mail or whatever is deemed appropriate.

It is contemplated that a certified testing laboratory may be added to the vehicle of FIG. 1 or to accompany the vehicle where large numbers of donors are processed so that at least those results that are clearly negative can promptly be made available and reduce the number of containers that must be transported to a more comprehensive testing laboratory.

To provide a suitable vehicle for a collection station, it is desirable to have a locker 24 for valuables such as purses. A garment hanging area 26 may be provided for outer clothes that may possibly serve to hide containers of liquid or other substances. This precaution aids in preventing liquids or other substances from being taken into the privacy rooms 12 to be placed in the urine containers rather than a proper urine specimen.

Because the width of the vehicle 10 is limited to legal highway widths, the person occupying reception station 20 who is located adjacent the single access aisle to the four privacy rooms, can effectively police the proper procedures which are intended to prevent cheating. Entrance to and exit from the vehicle may be by a single door 28. If the length of the vehicle is sufficient, a seating area 30 may be provided inside the vehicle; however, the release of sterile containers should not occur until the movements of the donor can be fully monitored.

At the moment of assigning a sterile container to a donor, the picture-identification of the donor is made and a name and or identification mark is permanently attached to the container.

Prior to handing the container to the donor, exterior clothing is hung in a storage area 26 and handbags or other valuable articles are placed in one of the security lockers 24. Thereafter, the donor with the container is directed into a privacy room 12. When the donor exits with the filled container, a seal is attached to the container cover and initialed by donor. The container may then be placed in a further secure package, such as a tamper-proof plastic bag which is then suitably sealed, and for subsequent transfer to the testing laboratory. By this procedure, a reasonably secure urine collection method ma be provided without requiring observation by a collection site person during the collection of the urine specimen.

Figure 2:
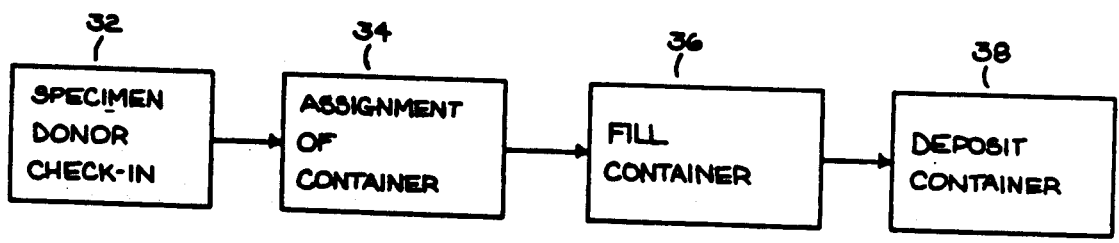
FIG. 2 is a block diagram of the steps employed in the method according to the present invention.

With reference to FIG. 2, the process involves a first step of directing the donor to appear at the parking location for the mobile collection unit 10 as indicated in block 32. If there is no waiting line, an empty container is assigned to the donor as indicated in block 34. At that time, the donor is picture-identified and the container appropriately labeled as for example, by a bar code or other machine readable identifier.

When the donor has removed such outer clothing as may be required and valuables such as a purse or the like placed in the lockable storage unit, then the donor is permitted to enter one of the privacy rooms as indicated by block 36.

After the specimen container has been filled and presented to the collection site person, the container is brought to the counter near the sink 16 where a closure seal is applied and initialed by the donor. The sealed container is then placed in the custody of the collection site person for temporary secure storage in the deposit receptacle 18 as indicated by block 38.

This process, by reason of the inherent size limitations of a road vehicle, has several advantages which contribute to a reasonably secure urine collection methodology that does not require observation and which offers extreme convenience of location. In addition, costly room construction or modification in existing buildings is eliminated. It is particularly advantageous where employers require urine collection only on an occasional basis.

Where the urine collection process is carried out in a motor home type vehicle as illustrated in FIG. 1 having a self contained driving engine, steering wheel 40 drive seat 42 and passenger seat 44, a unit having a length of 25 to 30 feet is preferred. A water supply tank of one hundred to two hundred gallons and a holding tank of one hundred twenty-five to two hundred fifty gallons would be adequate for some applications. Electricity may be supplied either by an on-board motor-generator set and/or extension cables from a fixed power source.

Figure 3:
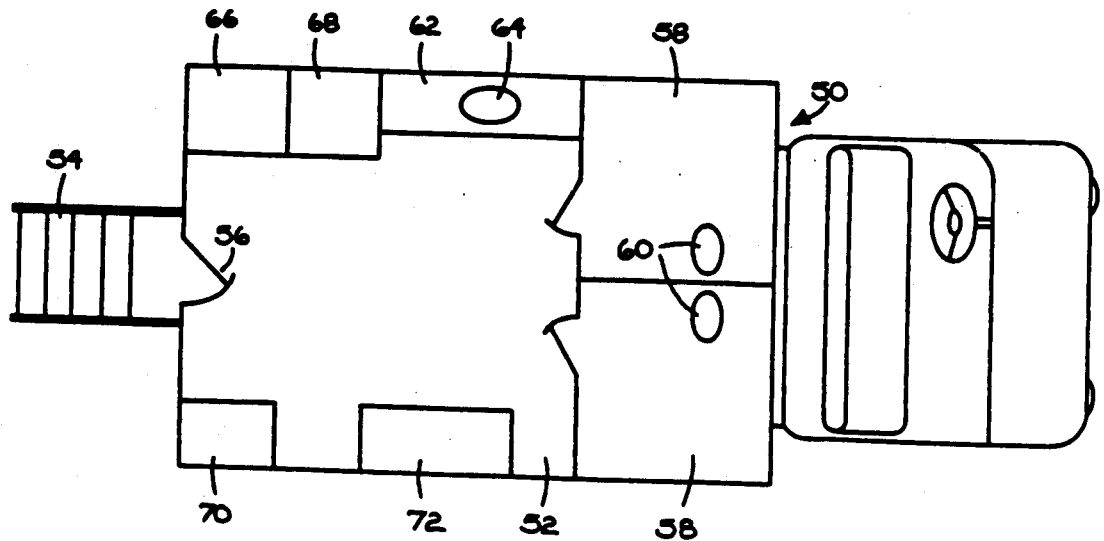
FIG. 3 is a top plan view of a small truck provided with two privacy rooms capable of being used in accordance with the present invention.

FIG. 3 illustrates the urine collection facility installed on a small truck 50 having a camper body 52 on the truck bed with the ladder 54 for entrance through a rear door 56 to an enclosure which has a pair of privacy rooms 58, each equipped with a receptacle 60 but not a sink. The counter 62 and sink 64 are between the back door 56 and the privacy rooms 58.

Outer garment storage area 66 and a lockable purse storage area 68 may be located at one side of the door 56 and the receptacle 70 for filled containers attached to the camper in a secure manner. A station 72 is provided for the collection site person.

Figure 4:
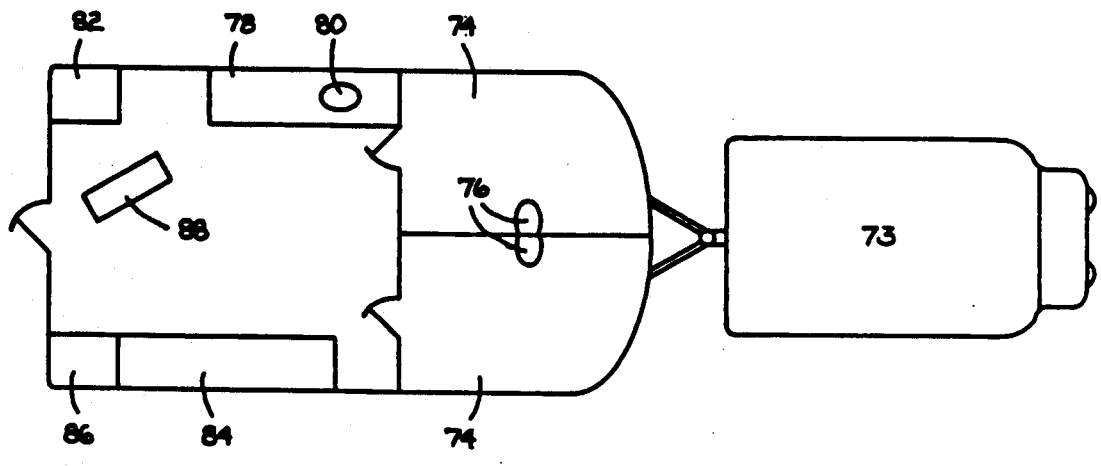
FIG. 4 is a top plan view of a small trailer towed by a towing vehicle which may be similar in size to the unit shown in FIG. 3.

Referring to FIG. 4, a similar layout may be provided in a trailer towable by a vehicle such as a pick-up truck or van 73. The trailer may have at least two privacy rooms 74 with receptacles 76 for receiving excess urine that is collected in a holding tank. The counter surface 78 for paperwork on and the sink 80 are located outside of the privacy rooms 74. The receptacle 82 for filled urine containers may be located on a wall or in the floor of the trailer with a suitable security arrangement. Outer garment storage area 84 and lockable purse storage area 86 may be located along the wall opposite the sink 84. A collection site person may use a podium or small desk 88 situated near the fill container receptacle 82.

Figure 5:
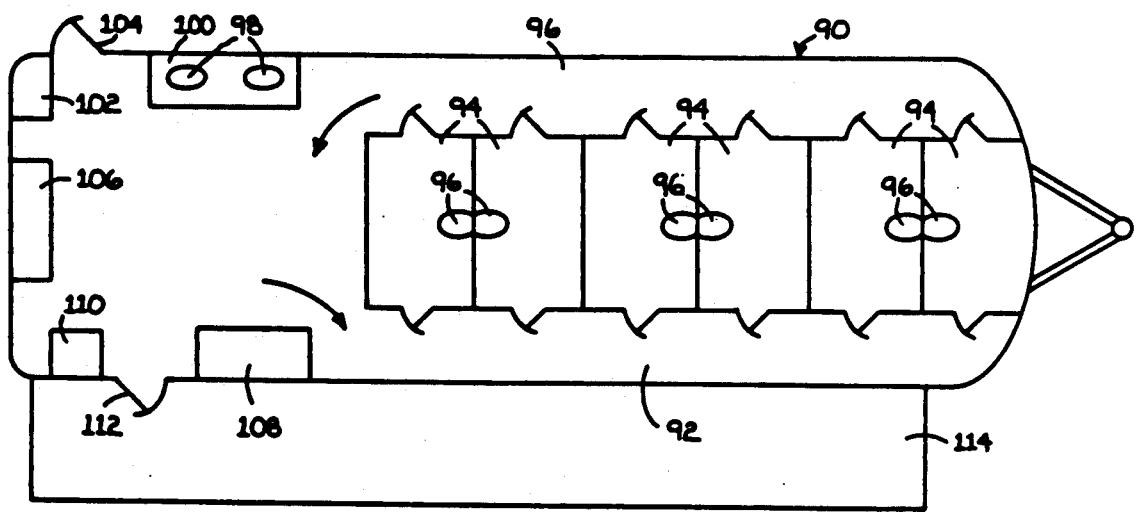
FIG. 5 is a top plan view of a large trailer having six privacy rooms centrally located with entrance and exit aisles on opposite sides.

FIG. 5 illustrates a longer trailer 90 which may be provided where the number of donors is relatively large. Instead of locating the privacy rooms along an outer wall, entry aisle 92 is provided on one side of a centrally located row of privacy rooms 94 each having a collection receptacle 96 for excess urine and the like.

Each privacy room 92 has an entry door opening into the entry aisle 92 and an exit door opening into the exit aisle 94. A pair of sinks 98 are located on opposite sides of a flat writing surface 100. The filled specimen containers are stored in a secure receptacle 102 near the exit door 104. Outer garment storage area 106 and lockable purse storage area 108 are located along the rear trailer wall and a side wall.

The reception station 110 is located at entry door 112 which may open onto a waiting area covered by an awning 114. The exit door 104 may be on the other side of the trailer 90 and a second collection site person should be stationed at that door to assure compliance with all regulations concerning accuracy of labelling and integrity of specimen.

Figure 6:
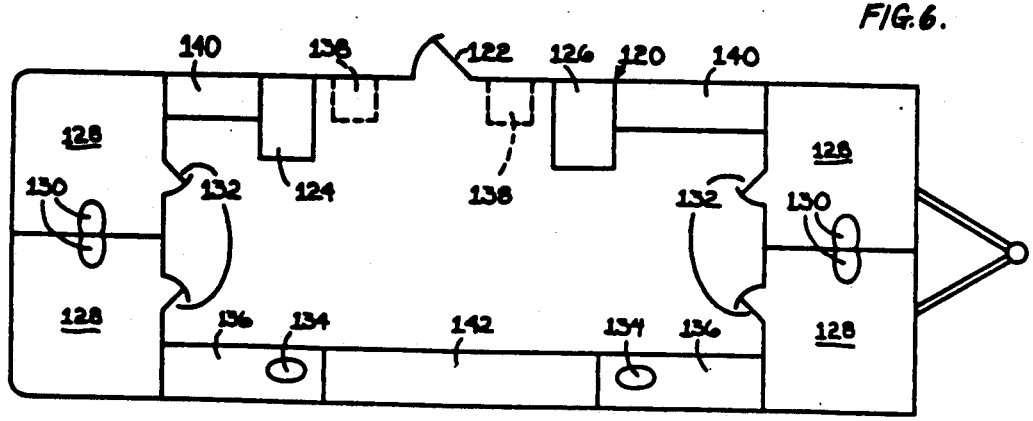
FIG. 6 is a top plan view of a large trailer having privacy rooms along the front and rear walls of the vehicle with stations for two collection site operators.

FIG. 6 illustrates yet a further embodiment utilizing a towable trailer 120. The trailer 120 may be similar to that shown in FIG. 5 and equipped with a centrally located door 122 with two stations 124 and 126 for collection site persons. At the rear of the trailer are two privacy rooms 128 with urine disposal devices 130 and doors 132 which are in close proximity to the collection site person at station 124. A sink 134 is located outside of the privacy rooms along with a flat surface 136 which is useful in sealing the specimen container and completing necessary paperwork. Thereafter, the container is placed in a receptacle 138 which provides short-term secure storage such as a U.S. Postal Service sidewalk mail box. Once a specimen container has been sealed and deposited in the receptacle 138, the specimen container is not accessible except by way of opening a locked door.

The receptacle 138 may be advantageously located beneath the floor with a side wall slot for dropping filled specimen containers into the lower receptacle. Removal of the containers may be accomplished only by unlocking a panel which may be either a floor panel or an exterior wall panel. Such a construction may be incorporated into any of the embodiments described above. A lockable compartment 140 for valuables is adjacent the station 124.

The forward end of the trailer has an identical layout and the same reference numerals are used to identify the corresponding parts. An outer garment closet or compartment 142 may be located along a wall opposite the door 122 and shared by donors using both of the facilities in the single trailer.

In this configuration, the space is arranged so that each collection site person can fully monitor the activities in connection with obtaining an unadulterated urine specimen. This will reduce the likelihood that switching of specimen containers can be effected since the trailers have walls without windows which open, therefore minimizing the likelihood of substitution of a foreign liquid for the donor urine specimen. Heating and cooling are provided by the normal means provided on motor homes or towed trailers in accordance with the climate conditions where the vehicle is used.

While several embodiments of the invention have been illustrated, other variations and modifications utilizing the spirit of the invention may be utilized. All changes which fall within the scope of the appended claims are intended to be covered thereby.

I claim:

1. A method of collecting, without observation and in a container, urine specimens that are to be analyzed for illegal drugs comprising:

providing a highway vehicle having at least two privacy rooms each having a receptacle for disposal of urine and free of access to substances that can be used for the purpose of altering laboratory test results from the results justified by the unadulterated urine specimen of the donor, a secure area for temporary storage for filled urine containers and a reception station for a collection site person;

transporting said vehicle to a predetermined location;

directing a urine donor to said predetermined location and to the reception area of said vehicle wherein each donor is given an empty urine collection container;

marking the empty container with a unique identification indicator;

carrying the empty container into a privacy room;

filling the container with the urine sample by the donor while the donor is in one of said privacy rooms and unobserved;

returning the urine filled container to the collection site person where the container is sealed in the presence of the donor and thereafter deposited in said secure area for temporary storage; and removing the urine containers from said temporary storage to a testing location under the controlled custody.

2. A method of collecting in a container urine specimens that ar to be analyzed without observation comprising:

providing a highway vehicle having:
at least two privacy rooms each having a receptacle for disposal of urine and free of access to substances that can be used for the purpose of altering laboratory test results from the results justified by the urine specimen of the donor;
a sink and writing surface positioned outside of the privacy rooms;
a first storage area for outer garments;
a second lockable storage area for valuables including purses that are not permitted in the privacy rooms;
a secure area for temporary storage of filled urine containers; and
a reception station for a collection site person located near a door to control entry of persons to the vehicle and near a supply of empty containers;

transporting said vehicle to a predetermined location;

directing a urine donor to said predetermined location and to said vehicle reception area where each donor is given a urine collection container;

marking the container with a unique identification after the donor has supplied to the collection site person picture identification;

placing any outer garments in said first storage area and valuable articles in said lockable compartment before giving custody of the marked containers to said donor;

observing the donor as the donor enters one of said privacy rooms;

filling the container with an unadulterated urine sample while the donor is in one of said privacy rooms and unobserved;

returning the urine filled container to the collection site person;

sealing the container in the presence of the donor and collection site person;

thereafter depositing said container in said secure area for temporary storage;

transporting the vehicle from said predetermined location and subsequently removing the urine containers from said secure storage for transmission to a testing location under controlled custody.

3. A method of collecting in a container urine specimens sequentially form a plurality of donors for subsequent analysis for illegal drugs in a vehicle having:

a frame for a floor, side walls and a roof supported by ground engaging wheels;

a supply of specimen containers;

at least two privacy rooms each having a receptacle for disposal of urine and free of available substances that can be used buy a donor to adulterate or as a substitute for urine to be collected in one of the specimen containers;

a sink outside of the privacy rooms and a writing surface for facilitating sealing of a urine filled specimen container and completion of appropriate marking of the container;

an area for temporary storage of urine filled specimen containers that is sufficiently secure to prevent unauthorized access to said containers;

a collection site person station located in proximity to said specimen container supply and said storage area for filled specimen containers; and an outer garment storage and article storage area located in position under the observation and control of a person at said collecting site station;

said method including the steps of:

transporting the vehicle to a temporary parking area and after the collection period is complete, moving the vehicle to a second temporary parking area;

directing donors to the vehicle while the vehicle is parked;

identifying the donor and marking an empty container with donor identification indicia;

removing from the donor's possession articles which can produce a false analysis of the donor's own urine;

thereafter giving the marked container to the donor who fills the container while in one of said privacy rooms and returns the filled container to a collection site person for sealing and marking he container in the presence of said donor;

then placing said filled container in said temporary storage area until a plurality of containers are available for simultaneous removal and transport to a testing facility.

* * * * *